United States Patent
Houben (10) Patent No.: US 7,099,714 B2
(45) Date of Patent: Aug. 29, 2006

(54) BIOMEDICAL SIGNAL DENOISING TECHNIQUES

(75) Inventor: Richard P. M. Houben, Lanaken (BE)

(73) Assignee: Medtronic, Inc., Minneapolis, MN (US)

( * ) Notice: Subject to any disclaimer, the term of this patent is extended or adjusted under 35 U.S.C. 154(b) by 505 days.

(21) Appl. No.: 10/403,915

(22) Filed: Mar. 31, 2003

(65) Prior Publication Data

US 2004/0193065 A1 Sep. 30, 2004

(51) Int. Cl.
*A61N 1/37* (2006.01)
(52) U.S. Cl. .......................... 600/509; 607/27
(58) Field of Classification Search ................. 607/27; 600/508–510
See application file for complete search history.

(56) References Cited

U.S. PATENT DOCUMENTS

| | | | | |
|---|---|---|---|---|
| 5,619,998 | A * | 4/1997 | Abdel-Malek et al. | 600/437 |
| 5,730,142 | A | 3/1998 | Sun et al. | |
| 5,755,739 | A | 5/1998 | Sun et al. | |
| 5,778,881 | A | 7/1998 | Sun et al. | |
| 5,782,888 | A | 7/1998 | Sun et al. | |
| 6,324,421 | B1 | 11/2001 | Stadler et al. | |
| 6,393,316 | B1 | 5/2002 | Gillberg et al. | |
| 6,397,100 | B1 | 5/2002 | Stadler et al. | |
| 6,438,419 | B1 | 8/2002 | Callaway et al. | |
| 6,440,082 | B1 | 8/2002 | Joo et al. | |
| 2003/0185408 | A1* | 10/2003 | Causevic et al. | 381/94.1 |

OTHER PUBLICATIONS

Fokapu, O. et al. "Denoising EMG and EEG for Monitoring Small Animal Models During NMR Experiments," *IEEE, Proceedings of the 23rd Annual Int'l Conference of the IEEE Engineering in Medicine and Biology Society, 2001 Conference Proceedings (EMBS)*,Istanbul, Turkey, vol. 1 of 4, Conf. 23, p. 1824-27 (Oct. 25, 2001).

Tikkanen, P.E., "Nonlinear Wavelet and Wavelet Packet Denoising of Electrocardiogram Signal," *Biol. Cybern.*, vol. 80, No. 4, p. 259-267 (Apr. 1999).

Zhu, Hailong et al., "Improving De-Noising by Coefficient De-Noising and Dyadic Wavelet Transform," *Pattern Recognition, 2002, Proceedings 16th Int'l Conf. On Quebec City, CA; LDS Alamitos, CA, IEEE Comput. Sci.*, p. 273-276 (Aug. 11, 2002).

Cai, Chunsheng et al., "Different Discrete Wavelet Transforms Applied to Denoising Analytical Data," *J. Chem. Inf. Comput. Sci.*, vol. 38, No. 6, p. 1161-1170 (Dec. 1998).

Khene, M.F. et al. "Adaptive Seismic Compression by Wavelet Shrinkage," *Proceedings of the Tenth IEEE Workshop on Statistical Signal and Array Processing*, Piscataway, NJ, p. 544-548 (2000).

* cited by examiner

*Primary Examiner*—Scott M. Getzow
(74) *Attorney, Agent, or Firm*—Michael C. Soldner; Girma Wolde-Michael (57) ABSTRACT

The invention is directed to denoising techniques for electrograms, or other biomedical signals, in which wavelet transformations are used in the denoising process. For example, an electrogram can be represented by a finite set of wavelets which comprise a decomposition of the electrogram in the scale-time domain. In accordance with the invention, an electrogram can be transformed into a set of wavelets, and thresholding can be performed on the wavelets to eliminate noise while preserving the information of the electrogram. Different thresholds can be used for the wavelets in different scales for improved denoising results. If a respective threshold exceeds a wavelet coefficient, the wavelet coefficient is reduced. Following the thresholding process, the wavelets can be converted into a denoised electrogram, which can be analyzed or processed. In this manner, wavelet transformations can be exploited for effective electrogram denoising.

34 Claims, 5 Drawing Sheets

BIOMEDICAL SIGNAL DENOISING TECHNIQUES

TECHNICAL FIELD

The invention relates to medical devices, and more particularly to signal processing of electrograms or other biomedical signals.

BACKGROUND

A wide variety of medical devices have been developed to monitor patient conditions and possibly deliver therapy to the patient. In some cases, the medical devices comprise external medical devices that are used to monitor a patient. In other cases, the medical devices are implantable medical devices (IMDs) that are surgically implanted inside a patient for short or long term therapy. Telemetry can be used to communicate sensed electrograms from one medical device to another medical device, e.g., from an IMD to an external medical device.

One common example of an IMD is a pacemaker. A pacemaker typically includes one or more pacing and sensing leads for delivery of pacing pulses to a patient's heart. Another example of an IMD is a combination pacemaker-cardioverter-defibrillator. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Medical devices, including IMDs and external medical devices, often sense and record electrograms of a patient. Electrograms refer to signals which represent recorded changes in electric potential of the patient. Examples of electrograms include electrocardiograms, i.e., recorded electrical potentials associated with a patient's heart; and electroencephalograms, i.e., recorded electrical potentials associated with a patient's brain. Other more specific examples of electrograms include atrial electrograms, coronary sinus (CS) electrograms, esophageal electrograms, high right atrial (HRA) electrograms, His bundle electrograms, intraatrial electrograms, intracardiac electrograms, right ventricular electrograms, right ventricular apical electrograms, sinus node electrograms, and the like.

Signal processing of electrograms is a common challenge in the medical field. In particular, it is often necessary to identify specific features of an electrogram so that medical events can be identified in the patient, such as arrhythmias in the patients heart. However, in many cases, signal noise can complicate analysis of electrograms. For this reason, denoising techniques are desirable in order to reduce or eliminate noise from electrograms.

SUMMARY

In general, the invention is directed to denoising techniques for electrograms in which wavelet transformations are used in the denoising process. For example, an electrogram can be represented by a finite set of wavelets which comprise a decomposition of the electrogram in the scale-time domain. In accordance with the invention, an electrogram can be transformed into a set of wavelets, and thresholding can be performed on the wavelets to eliminate noise but preserve the information of the electrogram. In particular, different thresholds can be established for the wavelet coefficients in different scales for improved denoising results. If a respective threshold exceeds a wavelet coefficient, the wavelet coefficient is reduced, e.g., by setting the coefficient to zero. Following the thresholding process, the wavelets can be converted into a denoised electrogram, which can be analyzed or processed.

In one embodiment, the invention provides a method comprising transforming an electrogram into a set of wavelets, the set of wavelets including different subsets of wavelets for different scales, comparing first wavelet coefficients of the wavelets in a first subset to a first threshold and comparing second wavelet coefficients of the wavelets in a second subset to a second threshold, the second threshold being different than the first threshold. The method can also include reducing one or more of the first wavelet coefficients that are less than the first threshold, and reducing one or more of the second wavelet coefficients that are less than the second threshold. In most cases, reduction of a wavelet coefficient comprises setting the wavelet coefficient to zero.

In another embodiment, the invention provides a medical device comprising a wavelet transform unit to transform an electrogram into a set of wavelets, the set of wavelets including different subsets of wavelets for different scales, and a wavelet denoising unit to compare first wavelet coefficients of the wavelets in a first subset to a first threshold, compare second wavelet coefficients of the wavelets in a second subset to a second threshold, the second threshold being different than the first threshold, reduce one or more of the first wavelet coefficients that are less than the first threshold, and reduce one or more of the second wavelet coefficients that are less than the second threshold.

In another embodiment, the invention provides a system comprising a first medical device to record electrograms and perform denoising of the electrograms by transforming an electrogram into a set of wavelets, the set of wavelets including different subsets of wavelets for different scales, comparing first wavelet coefficients of the wavelets in a first subset to a first threshold, comparing second wavelet coefficients of the wavelets in a second subset to a second threshold, the second threshold being different than the first threshold, reducing one or more of the first wavelet coefficients that are less than the first threshold, and reducing one or more of the second wavelet coefficients that are less than the second threshold. The system can also include a second medial device to perform threshold estimation to establish the first and second thresholds and send the first and second thresholds to the first medical device.

In another embodiment, the invention provides a computer readable medium comprising computer readable instructions that when executed transform an electrogram into a set of wavelets, the set of wavelets including different subsets of wavelets for different scales, compare first wavelet coefficients of the wavelets in a first subset to a first threshold, compare second wavelet coefficients of the wavelets in a second subset to a second threshold, the second threshold being different then the first threshold, reduce one or more of the first wavelet coefficients that are less than the first threshold, and reduce one or more of the second wavelet coefficients that are less than the second threshold.

In another embodiment, the invention provides an apparatus comprising means for transforming an electrogram into a set of wavelets, the set of wavelets including different subsets of wavelets for different scales, means for comparing first wavelet coefficients of the wavelets in a first subset to a first threshold, and means for comparing second wavelet coefficients of the wavelets in a second subset to a second threshold, the second threshold being different then the first threshold. The apparatus can further comprise means for reducing one or more of the first wavelet coefficients that are less than the first threshold, and means for reducing one or more of the second wavelet coefficients that are less than the second threshold.

In another embodiment, the invention provides a system comprising means for transforming an electrogram into a set of wavelets, the set of wavelets including different subsets of wavelets for different scales, means for comparing first wavelet coefficients of the wavelets in a first subset to a first threshold, means for comparing second wavelet coefficients of the wavelets in a second subset to a second threshold, the second threshold being different then the first threshold, means for reducing one or more of the first wavelet coefficients that are less than the first threshold and means for reducing one or more of the second wavelet coefficients that are less than the second threshold. The system can also include means for selecting the first and second thresholds prior to transforming the electrogram into the set of wavelets.

In another embodiment, the invention provides a method comprising comparing first wavelet coefficients for first-scale wavelets representative of an electrogram to a first threshold, comparing second wavelet coefficients for second-scale wavelets representative of the electrogram to a second threshold, reducing the first wavelet coefficients that are less than the first threshold, and reducing the second wavelet coefficients that are less than the second threshold, the second threshold being different than the first threshold.

In another embodiment, the invention provides a method comprising transforming a biomedical signal into a set of wavelets, the set of wavelets including different subsets of wavelets for different scales, and comparing first wavelet coefficients of the wavelets in a first subset to a first threshold. The method can further include comparing second wavelet coefficients of the wavelets in a second subset to a second threshold, the second threshold being different then the first threshold, reducing one or more of the first wavelet coefficients that are less than the first threshold, and reducing one or more of the second wavelet coefficients that are less than the second threshold.

Some of the inventive elements of the present invention include, for example, the denoising techniques described herein are easy to implement from a computational standpoint, relative to some conventional denoising techniques. Moreover, because the invention is relatively easy to implement from a computational standpoint, it is well suited for use in implanted medical devices where computational resources are limited and power consumption is a concern.

As an added aspect, setting insignificant noise related coefficients to zero can compress the electrogram without losing the significant information of wavelets having large coefficients, e.g., that coincide with the largest slopes in the electrogram signal. The denoising techniques can be particularly useful in implantable cardiac signal loops or other types of implantable diagnostic loop recorders that make use of subcutaneous electrodes for electrogram sensing. Such devices typically record significant amounts of electrogram noise caused by the patients pectoral muscles or other muscles or tissue. In accordance with the invention, however, such noise can be identified and eliminated by wavelet thresholding making use of different thresholds for different wavelet scales.

The details of one or more embodiments of the invention are set forth in the accompanying drawings and the description below. Other features and inventive aspects of the invention will be apparent from the description and drawings, and from the claims.

DETAILED DESCRIPTION

The invention is directed to denoising techniques for electrograms, or other types of biomedical signals, in which wavelet transformations are used in the denoising process. For example, an electrogram can be represented by a finite set of wavelets which comprise a decomposition of the electrogram in the scale-time domain. In accordance with the invention, an electrogram can be transformed into a set of wavelets, and thresholding can be performed on the wavelets to eliminate noise but preserve the information of the electrogram. Following the thresholding process, the wavelets can be converted into a denoised electrogram. Although many details of the invention are described in the context of electrograms, the techniques can be equally applicable to denoising of other types of biomedical signals.

The set of wavelets include subsets of wavelets for each of a plurality of different scales. However only some of the wavelets include the majority of information indicative of the electrogram, and others primarily include noise. Thus, by setting wavelet coefficients to zero for those wavelets that primarily include noise, substantial reductions in noise can be achieved without eliminating the information indicative of the electrogram.

In order to improve denoising, different thresholds can be established specifically for the different subsets of wavelets associated with each scale. In other words, the thresholds vary for wavelets in different scales. If a wavelet coefficient exceeds a respective threshold associated with the given subset of wavelets, the wavelet coefficient remains unchanged. However, if the respective threshold exceeds the wavelet coefficient, the wavelet coefficient is reduced, e.g., and typically set to zero. The denoised set of wavelets can then be converted into a denoised electrogram. In this manner, wavelet transformations can be exploited for effective electrogram denoising.

In order to define the thresholds at the various wavelet scales, a medical procedure can be performed. In particular, a physician instructs the patient to assume certain positions to trigger noise in the electrograms. The physician can then analyze the electrograms, and make adjustments to one or more of the thresholds, at different scales, in order to improve denoising. Adjustments to the thresholds can occur automatically, as a result of execution of a thresholding algorithm, or can be entered manually by a physician. In either case, the medical procedure to define the thresholds can be particularly useful with implantable diagnostic loop recorders that make use of subcutaneous electrodes for electrogram sensing. For example, noise caused by the patients pectoral muscles (or other muscles or tissue) can be identified by instructing the patient to assume the certain positions, and the thresholds can be adjusted to compensate for such noise.

Wavelet transforms are particularly useful in analysis of non-stationary signals because wavelet transforms provide an alternative to the classical short time Fourier transform (STFT) and Gabor transform. The wavelet transform is typically a linear operation that decomposes a signal into components that appear at different scales (or resolutions). A mother wavelet comprises a zero average function $\Psi \in L^2(R)$ (finite energy):

$$\int_{-\infty}^{\infty} \Psi(t)dt = 0 \text{ (Admissibility condition)} \qquad \text{EQUATION 1}$$

Equation 1 can be normalized $\|\Psi\|=1$, and centered round $t=0$. Then, a set of wavelets can be obtained by scaling and translation of the mother wavelet $\Psi$ by s, and translation by u:

$$\Psi_{u,s}(t) = \frac{1}{\sqrt{s}} \Psi\left(\frac{t-u}{s}\right) \qquad \text{EQUATION 2}$$

As used in this disclosure, the phrase "set of wavelets" generally refers to all of the wavelets generated from a mother wavelet function to represent the electrogram. The set of wavelets includes wavelets at a number of different scales. The phrase "subset of wavelets" refers to the wavelets of a particular scale. Thus, different subsets of wavelets are associated with each scale, and all of the subsets of wavelets at every scale comprise the set of wavelets generated from the mother wavelet function. Put another way, a set of wavelets includes first-scale wavelets, second-scale wavelets, third-scale wavelets, and so forth.

Wavelet analysis allows the use of coarse wavelets where more precise low-frequency information is needed, and fine wavelets where high-frequency information is needed. In analogy to the STFT, the wavelet transform is defined as the sum over all time of the signal multiplied by scaled, shifted versions of the wavelet function. For functions $f \in L^2(R)$ the wavelet transform at time u and scale s is defined as:

$$Wf(u, s) = <f, \Psi_{u,s}> = \int_{-\infty}^{\infty} f(t)\Psi^*\left(\frac{t-u}{s}\right)dt \qquad \text{EQUATION 3}$$

This type of transform satisfies energy conservation. With decrease of scale 's,' the support for the wavelet decreases and the wavelet becomes more sensitive to high-frequency components of the signal, enhancing finer grain details of the signal. An increase in scale, on the other hand, provides more emphasis on the coarse structure of the signal. The result of the wavelet transform can be defined in the scale-time plane. The wavelet transform can be rewritten as a convolution product:

$$Wf(u, s) = \int_{-\infty}^{\infty} f(t)\Psi^*\left(\frac{t-u}{s}\right)dt = f * \bar{\Psi}_s(u), \qquad \text{EQUATION 4}$$

$$\text{where } \bar{\Psi}_s(t) = \frac{1}{\sqrt{s}}\Psi^*\left(\frac{-t}{s}\right) \qquad \text{EQUATION 5}$$

The Fourier transform of $\bar{\Psi}_s(t)$ is:

$$\hat{\bar{\Psi}}(\omega) = \sqrt{s}\hat{\Psi}^*(s\omega) \qquad \text{EQUATION 6}$$

$\hat{\Psi}$ is similar to the transfer function of a band-pass filter, so the convolution can compute the wavelet transform with dilated impulse response band-pass filters.

Many electrograms, including electrocardiograms, carry most important information at their singularities and sharp deflections. The wavelet transform is particularly well adapted to characterize transient phenomena or singularities, because wavelet transforms decompose signals into building blocks well localized in time and frequency. The wavelet transform can focus on localized signal structures with a zooming procedure that progressively reduces the scale parameter s. A measure of local regularity of the signal is provided by the decay of the wavelet transform amplitude across its scales. Singularities can be detected by following the wavelet transform local maxima at fine scales.

$$|Wf(u,s)| \leq As^{\alpha+1/2} \qquad \text{EQUATION 7}$$

From Equation 7, one can derive:

$$\log_2|Wf(u,s)| \leq \log_2 A + (\alpha+\tfrac{1}{2})\log_2 s \qquad \text{EQUATION 8}$$

Figure 1:
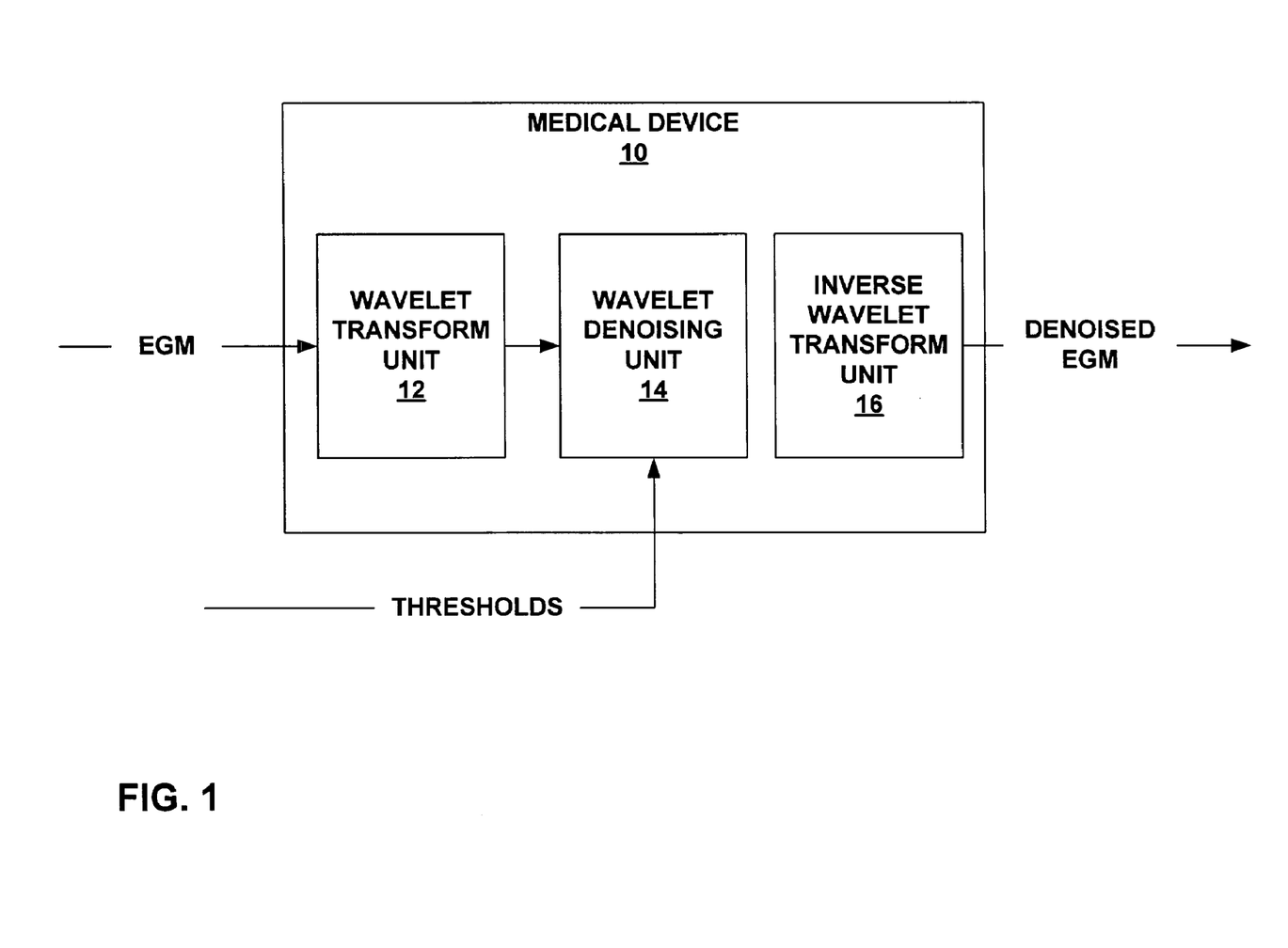
FIG. 1 is an exemplary block diagram of a medical device capable of wavelet-based denoising according to an embodiment of the invention.

FIG. 1 is an exemplary block diagram of a medical device 10 according to an embodiment of the invention. Medical device 10 may comprise any of a wide variety of medical devices used to analyze electrograms. For example, medical device 10 may comprise an implanted medical device (IMD) that includes various implanted electrodes (not shown) that are used for sensing the electrograms. Alternatively, medical device 10 may comprise an external medical device that uses surface electrodes on a patient's skin to sense the electrograms. Also, medical device 10 can be an implanted or external device that measures electrograms via subcutaneous electrodes, such as a diagnostic loop recorder that makes use of electrodes implanted under the patients skin. In other cases, medical device 10 comprises an external device that receives sensed electrograms from another device, e.g., via telemetry. In any case, medical device 10 performs denoising techniques on electrograms using wavelet analysis as described herein.

In general, medical device 10 includes a wavelet transform unit 12, a wavelet denoising unit 14, and an inverse wavelet transform unit 16. These components can be implemented as either analog or digital components. For example, wavelet transform unit 12, wavelet denoising unit 14 and inverse wavelet transform unit 16 can comprise analog logic circuits such as dynamic translinear (DLT) circuits, or can comprise digital logic or software implemented algorithms. In addition, various hardware/software combinations can be used to realize the different units. If wavelet transform unit 12, wavelet denoising unit 14 and inverse wavelet transform unit 16 are implemented in digital hardware, an analog-to-digital converter (not shown in FIG. 1) can be used to convert a received analog electrogram to a digital electrogram, i.e., a stream of digital samples of the analog electrogram.

In some digital implementations, one or more of wavelet transform unit 12, wavelet denoising unit 14 and inverse wavelet transform unit 16 comprise software modules executing on a digital signal processor (DSP), or the like. In that case, a computer-readable medium comprises machine readable instructions that when executed perform the functionality associated with wavelet transform unit 12, wavelet denoising unit 14 and/or inverse wavelet transform unit 16. Moreover, the invention can be in programmable logic, or other types of hardware, software or firmware.

Wavelet transform unit 12 performs wavelet transformation on an electrogram (EGM) in order to generate the set of wavelets, which collectively include the information in the electrogram. For example, wavelet transform unit 12 can perform wavelet transformation using mathematical framework similar to that outlined above. In particular, the set of wavelets can be obtained by scaling and translating a selected mother wavelet. Wavelet transform unit 12 can comprise a set of dilated impulse response band-pass filters designed to perform the desired wavelet transformation on the electrogram. The set of wavelets generated by wavelet transform unit 12 include numerous wavelets at various different scale factors. In other words, different subsets of wavelets exist for each scale factor. The scale factors span from a coarse scale to fine scale.

The coarse scale wavelets provide a larger overall picture of the electrogram, but lack specific details of the electrogram. The fine scale wavelets provide a less complete picture of the electrogram, but include more detail. The coarse scale wavelets have a scale greater than or equal to 10 multiplied by the scale of the fine scale wavelet, although the invention is not necessarily limited in that respect.

Wavelet denoising unit 14 performs denoising on the wavelets by comparing wavelet coefficients of the different wavelets to thresholds. If a given wavelet coefficient exceeds a given threshold, the wavelet coefficient remains unchanged. However, if a given threshold exceeds a given wavelet coefficient, wavelet denoising unit 14 reduces that wavelet coefficient, e.g., typically by setting that wavelet coefficient to zero. In this manner, denoising can be achieved.

In order to improve denoising, wavelet denoising unit 14 applies different thresholds to different subsets of wavelets associated with each scale. In other words, the thresholds vary for wavelets in different scales. If wavelet denoising unit 14 determines that a wavelet coefficient exceeds a respective threshold associated with the given subset of wavelets, the wavelet coefficient remains unchanged. However, wavelet denoising unit 14 determines that a respective threshold exceeds the wavelet coefficient, the wavelet coefficient is reduced, e.g., and typically set to zero. The different thresholds can be programmed into wavelet denoising unit 14. For example, as described in greater detail below, a medical procedure can be performed to define the thresholds for effective denoising.

Inverse wavelet transform unit 16 transforms the denoised set of wavelets back into a denoised electrogram. In particular, inverse wavelet transform unit 16 receives the set of denoised wavelets from wavelet denoising unit 14, i.e., the set of wavelets including both wavelets for which wavelet coefficients were unchanged and wavelets for which wavelet coefficients were reduced. Inverse wavelet transform unit 16 performs the inverse of the transformation performed by wavelet transform unit 12 to generate the denoised electrogram. In this manner, wavelet transformations can be exploited for effective electrogram denoising.

In an electrocardiogram, most of the wavelet coefficients are small. The largest coefficients coincide with the largest slopes in the electrogram signal, and only those few coefficients are typically significant. The denoising techniques implemented by wavelet denoising unit 14 are generally based on removing the important characteristics of the electrogram from of the noise. By comparing the wavelet coefficients to predetermined thresholds (which vary from scale to scale), insignificant noise related coefficients can be identified and set to zero.

The denoising techniques described herein can provide certain advantages relative to conventional denoising techniques. In particular, denoising of wavelets is relatively easy from a computational standpoint. Moreover, as an added benefit, setting insignificant noise related coefficients to zero can compress the electrogram without losing the significant information of wavelets having large coefficients, e.g., that coincide with the largest slopes in the electrogram signal.

Because the invention is relatively easy to implement from a computational standpoint, it is well suited for use in implanted medical devices where computational resources are limited and power consumption is a concern. Moreover, the denoising techniques can be particularly useful in implantable cardiac signal loops or other types of implantable diagnostic loop recorders that make use of subcutaneous electrodes for electrogram sensing. Such devices typically record significant amounts of electrogram noise caused by the patients pectoral muscles, or the like. In accordance with the invention, however, such noise can be identified and eliminated by wavelet thresholding.

Figure 2:
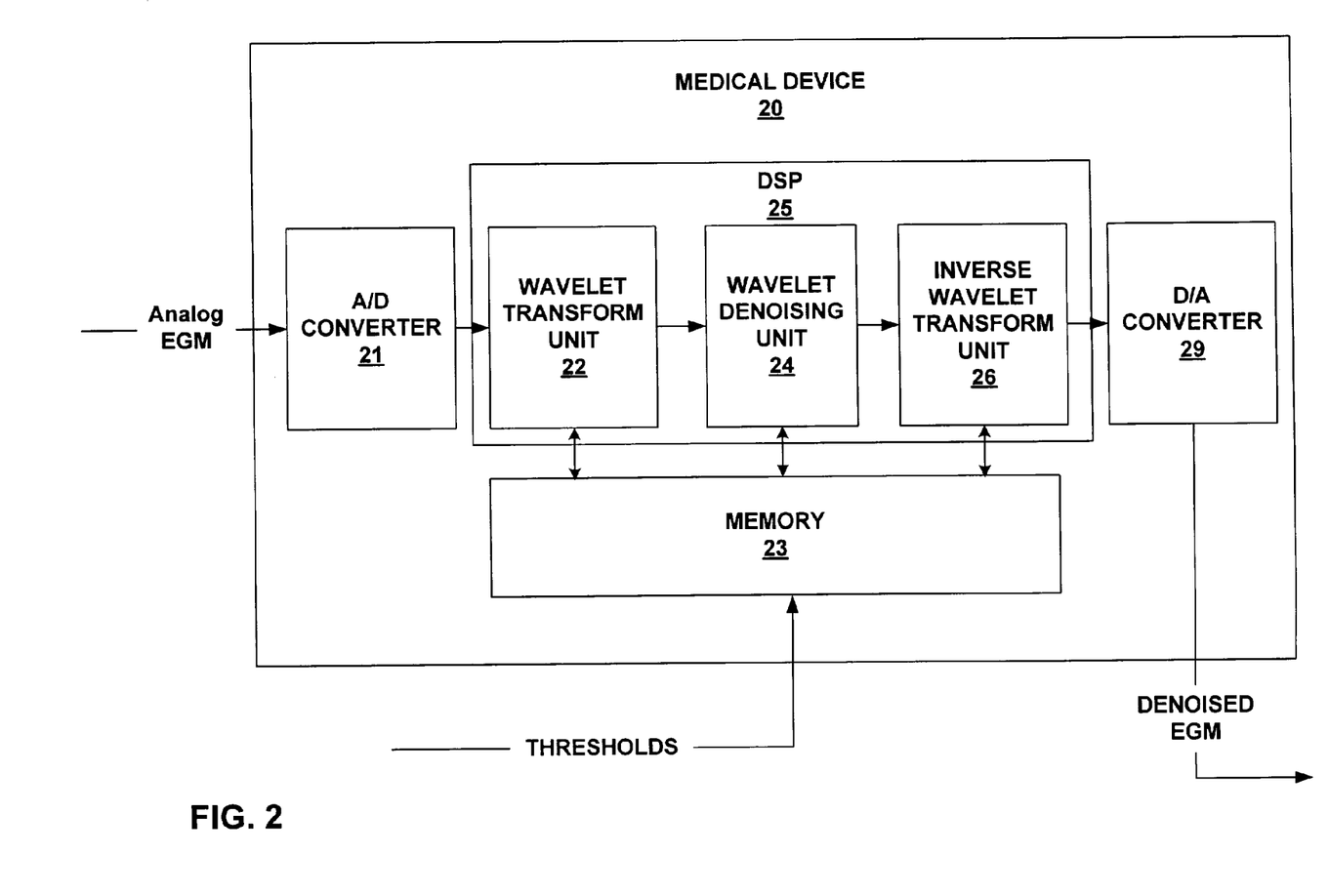
FIG. 2 is a more detailed block diagram of a medical device capable of wavelet-based denoising according to an embodiment of the invention in which denoising techniques are digitally implemented.

FIG. 2 is a more detailed block diagram of a medical device 20 according to an embodiment of the invention in which the denoising techniques are digitally implemented. Like medical device 10, medical device 20 may comprise any of a wide variety of medical devices used to analyze electrograms.

Medical device 20 includes an analog-to-digital (A/D) converter 21 that receives analog electrogram (EGM) and converts the analog electrogram to a digital electrogram, i.e., a stream of digital samples that represent the electrogram. Wavelet transform unit 22, wavelet denoising unit 24, and inverse wavelet transform unit 26 comprise software modules executing on DSP 25. For example, wavelet transform unit 22, wavelet denoising unit 24, and inverse wavelet transform unit 26 can comprise computer-readable instructions stored in memory 23, and invoked by DSP 25 to perform the denoising techniques described herein. For example, memory 23 can comprise random access memory (RAM), read-only memory (ROM), non-volatile random access memory (NVRAM), electrically erasable programmable read-only memory (EEPROM), flash memory, or the like.

Wavelet transform unit 22 performs wavelet transformation on the electrogram and generates the set of wavelets. In this example, wavelet transform unit 22 comprises a set of software-implemented dilated impulse response band-pass filters designed to perform the desired wavelet transformation on the electrogram according to the mathematical framework outlined above. The set of wavelets generated by wavelet transform unit 22 include numerous wavelets at various different scale factors.

Wavelet denoising unit 24 performs denoising on the wavelets by comparing wavelet coefficients to programmable thresholds. If a given wavelet coefficient exceeds a given threshold, the wavelet coefficient remains unchanged. However, if a given threshold exceeds a given wavelet coefficient, wavelet denoising unit 24 reduces that wavelet coefficient, e.g., typically by setting that wavelet coefficient to zero. Accordingly, the wavelet having a zero wavelet coefficient is essentially eliminated. In other cases, more complex non-zero reductions to some coefficients can be made. In any case, denoising can be achieved by such reductions of wavelet coefficients. The different thresholds associated with the different scales can be stored in memory 23, and can be selected or programmed during a medical procedure. More details of an exemplary medical procedure used to select the thresholds are provided below with reference to FIG. 5.

Inverse wavelet transform unit 26 transforms the denoised set of wavelets back into a denoised electrogram. In particular, inverse wavelet transform unit 26 performs the inverse of the transformation performed by wavelet transform unit 22 to generate the denoised electrogram. In this manner, wavelet transformations can be exploited for effective electrogram denoising. Digital-to-analog (D/A) converter 29 converts the denoised digital electrogram back to an analog signal for subsequent processing or analysis.

Figure 3:
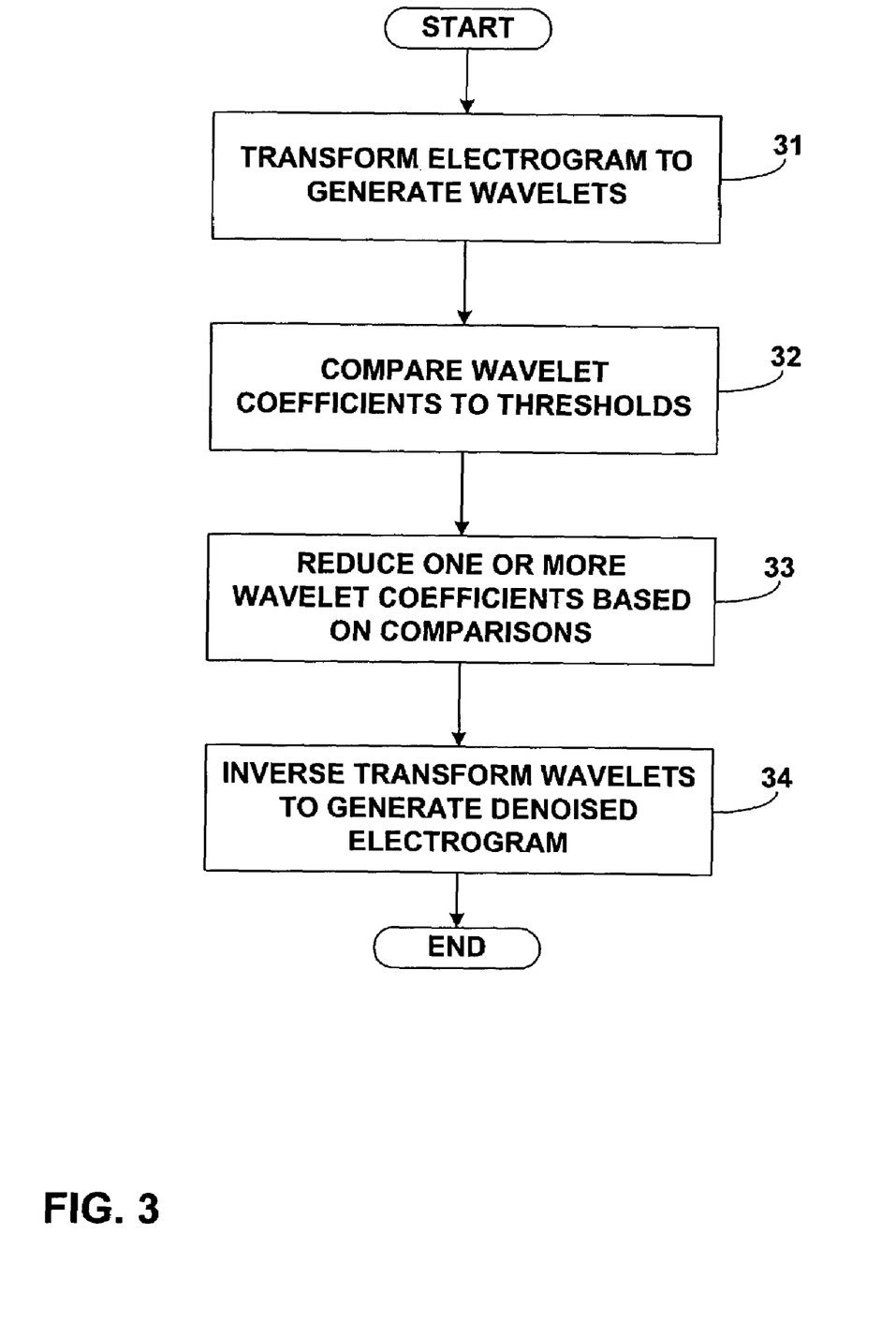
FIG. 3 is a flow diagram illustrating a denoising process in accordance with an embodiment of the invention.

FIG. 3 is a flow diagram illustrating a denoising process in accordance with an embodiment of the invention. For purposes of illustration, the process shown in FIG. 3 will be described from the perspective of medical device 10 of FIG. 1. As illustrated in FIG. 3, wavelet transform unit 12 transforms an electrogram to wavelets (31). Wavelet denoising unit 14 compares wavelet coefficients to thresholds (32), and reduces one or more wavelet coefficients based on these comparisons (33). Importantly, different thresholds are compared to the wavelet coefficients of different subsets of the wavelets corresponding to different scales of the wavelet transformation. The thresholds can be established for the different scales in order to promote improved denoising performance. Following reduction of one or more of the wavelet coefficients, inverse wavelet transform unit 16 performs an inverse transformation on the wavelets to generate a denoised electrogram (34), which can be analyzed or processed to promote medical therapy.

Figure 4:
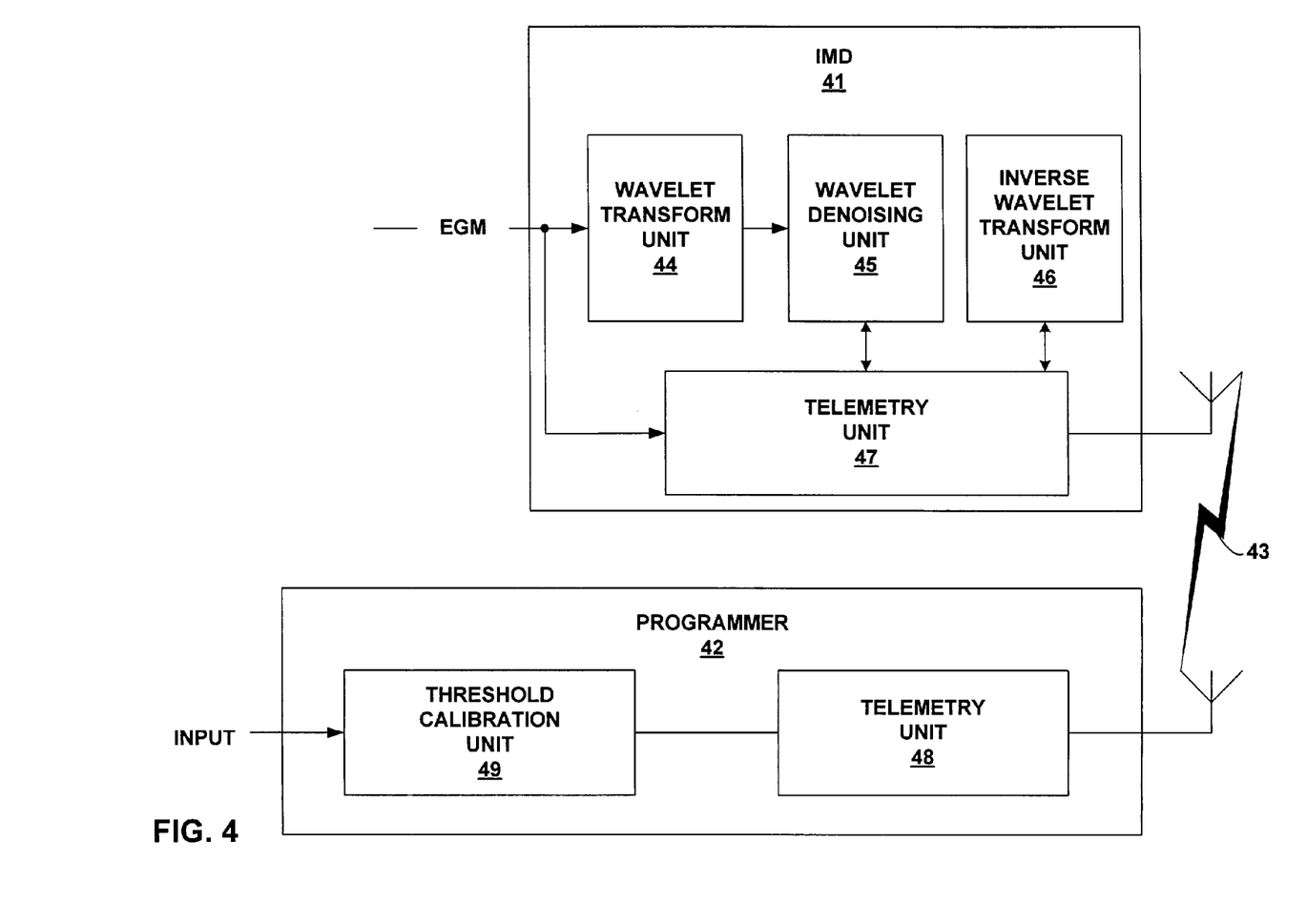
FIG. 4 is a block diagram of system, according to an embodiment of the invention, including first and second medical devices that communicate via telemetry to program denoising thresholds.

FIG. 4 is a block diagram of system 40 including first and second medical devices according to an embodiment of the invention. In one example, the first medical device comprises an implanted medical device (IMD) 41, such as an implanted diagnostic loop recorder that includes subcutaneous electrodes (not shown) for measuring electrograms of a patient, and the second medical device comprises a programmer 42. IMD 41 and programmer 42 communicate via telemetry signals 43. Programmer 42 can be used to program thresholds into IMD 41 for use during the denoising process. Again, in accordance with the invention, different thresholds are established for different scales of wavelets in order to improve the denoising process.

IMD 41 includes a wavelet transform unit 44, a wavelet denoising unit 45, and an inverse wavelet transform unit 46 that perform denoising of electrograms in a manner similar to the components illustrated in FIG. 1 and described above. However, prior to execution of the denoising process, the thresholds can be selected or defined for effective denoising performance. In particular, different thresholds are established for comparison with the wavelet coefficients of different subsets of the wavelets, e.g., at differing scales in the wavelet transformation.

IMD 41 includes a telemetry unit 47 that facilitates wireless communication of telemetry signals 43 with telemetry unit 48 of programmer 42. In particular, telemetry unit 47 of IMD 41 communicates sensed electrograms to telemetry unit 48 of programmer 42. Threshold calibration unit 49 of programmer 42 facilitates selection of the different thresholds to be applied at different wavelet scales. For example, threshold calibration unit 49 displays electrograms or denoised electrograms to a physician, and the physician provides input to threshold calibration unit 49 in order to select or modify these thresholds. Alternatively, adjustments to the thresholds can occur automatically as part of a thresholding algorithm executed by threshold calibration unit 49. In that case, the physician simply examines a denoised electrogram and either accept or reject the current thresholds. If rejected, adjustments can occur automatically as part of the thresholding algorithm.

Threshold calibration unit 49 can include a wavelet transform unit, a wavelet denoising unit and an inverse wavelet transform unit similar to those of IMD 41. Thus, when telemetry unit 47 receives a sensed electrogram, threshold estimation unit 49 can perform wavelet denoising techniques on the electrogram and display the denoised electrogram to a physician. The physician can then analyze the denoised electrogram and determine whether the electrogram is acceptable. If not, one or more of the thresholds can be adjusted by an algorithm executing on threshold calculation unit 49, or possibly by manual input by the physician. In particular, threshold calibration unit 49 adjusts the thresholds, and the denoising process is repeated. Once denoising is deemed acceptable by the physician, the thresholds can be communicated from telemetry unit 48 of programmer 42 to telemetry unit 47 of IMD 41. IMD 41 can the install the thresholds into wavelet denoising unit 45 for subsequent application in a denoising process of IMD 41.

In some cases, the physician instructs the patient to assume one or more different positions in order to purposely introduce noise into electrograms. The physician can inform programmer 42 (via telemetry) of such positions, and in response threshold calibration unit 49 adjust different thresholds, depending on the current electrogram being analyzed and the current position assumed by the patient. Such a technique can be particularly effective in defining thresholds when IMD 41 comprises an implanted diagnostic loop recorder that includes subcutaneous electrodes for measuring electrograms of a patient. In that case, noise associated with pectoral muscles (or other muscles or tissue) of the patient can be purposely introduced by patient movements or positioning. In still other cases, threshold estimation can be programmed manually by a physician, rather than automatic adjustments by an algorithm executing on threshold calibration unit 49.

Figure 5:
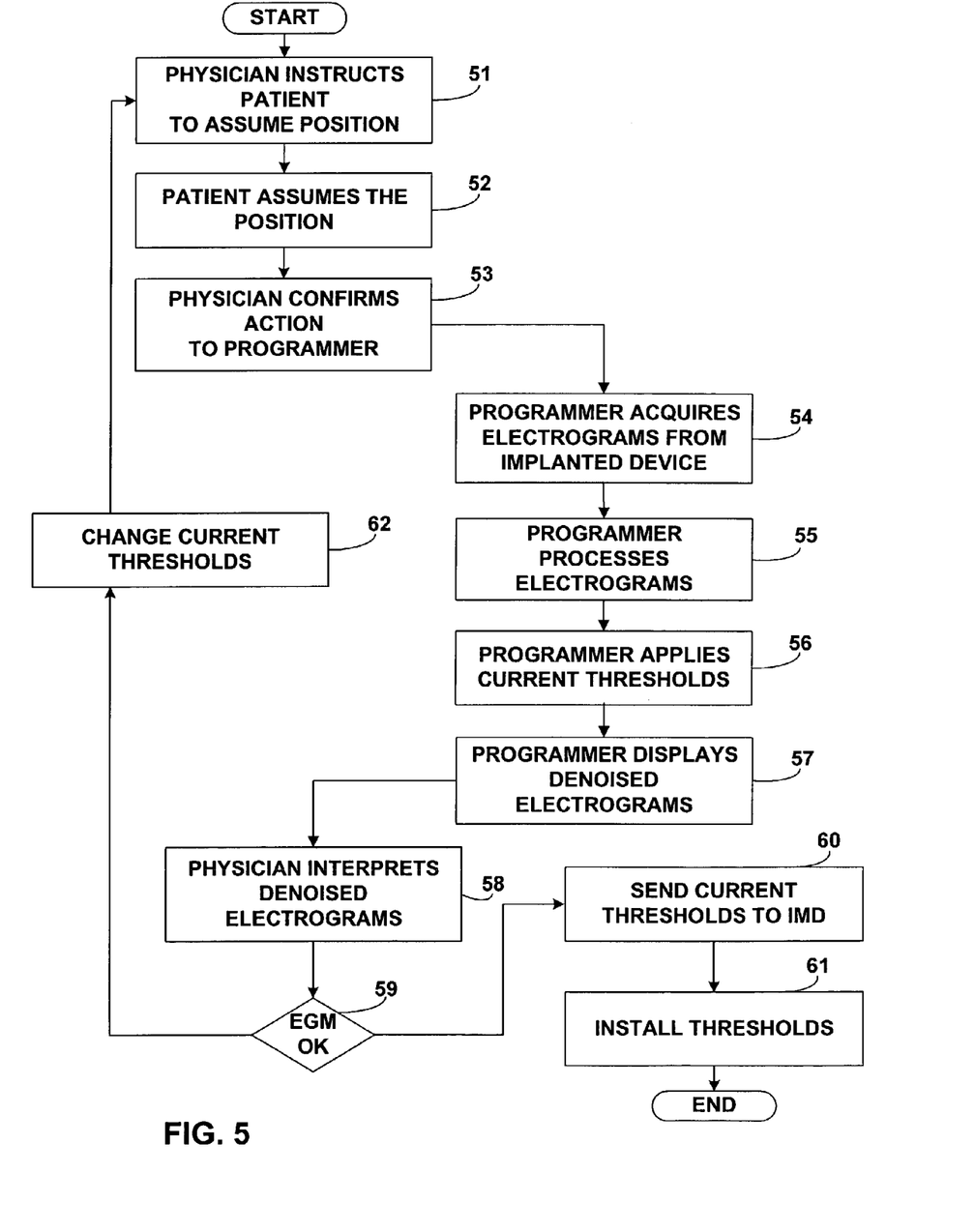
FIG. 5 is a flow diagram illustrating techniques for selecting thresholds applied in a denoising process according to the invention.

FIG. 5 is a flow diagram illustrating techniques for selecting thresholds to be applied in a denoising process. As shown in FIG. 5, a physician instructs a patient implanted with IMD 41 to assume a specific position that should introduce specific noise in an electrogram (51). Once the patient has assumed the position (52), the physician confirms the action with programmer 42 (53). Programmer 42 then acquires one or more sensed electrograms from IMD 41 (54).

Programmer 42 processes the electrograms (55), and applies current thresholds in a denoising process similar to that described herein (56). Programmer then displays denoised electrograms to the physician (57), and the physician interprets the denoised electrograms (58). If the physician determines that the denoised electrograms are acceptable (yes branch of 59), then programmer 42 sends the current thresholds to IMD 41 (60), and IMD 41 installs the current thresholds (61) for subsequent use in a denoising process performed by IMD 41.

However, if the physician determines that the denoised electrograms are unacceptable (no branch of 59), then the current thresholds are changed (62). For example, threshold calibration unit 49 can apply an algorithm to automatically adjust the thresholds, e.g., in response to a physician's input that the current denoised electrogram are unacceptable. Such adjustments can be non-linear, in that some thresholds are adjusted differently than others for improved denoising performance. Alternatively, the physician can manually enter new thresholds or manually adjust one or more of the current thresholds, e.g., via telemetry with programmer 42. In any case, the process is then repeated with the new current thresholds, and continues in an iterative fashion until acceptable thresholds are established. Moreover, in some cases, the process can be subsequently repeated with the patient assuming different positions. In that case, the threshold algorithm executing on threshold calibration unit 49 can be designed to pay close attention to specific thresholds when the patient assumes particular positions.

In some embodiments, the process is automated such that the physician only confirms that the patient has assumed the position. In other words, programmer 41 can be designed to automatically adjust one or more of the thresholds, without requiring the physician to make threshold selections. Again, in that case, a thresholding algorithm for adjusting the thresholds can be executed in threshold calibration unit 49. The physician confirms patient positioning to programmer 42, and then reviews and either accepts or rejects the denoised electrogram.

A number of embodiments of the invention have been described. However, one skilled in the art will appreciate that the invention can be practiced with embodiments other than those disclosed. For example, other types of mother wavelet functions can be used to generate the respective wavelets which are used in electrogram analysis. The invention can find application for denoising of a wide variety of different types of electrograms. In addition, the invention can find application for denoising of a wide variety of different types of biomedical signals including but not limited to electrograms measured via external sensors, electrograms measured via implanted sensors, a signals measured by one or more a biomedical sensor, chronic or acute signals, or any other biomedical signal that require denoising.

Also, the invention can be implemented in software, hardware, firmware, or the like. Example hardware implementations include implementations within an application specific integrated circuit (ASIC), a field programmable gate array (FPGA), a programmable logic device, specifically designed hardware components, one or more processors, or any combination thereof. If implemented in software, a computer readable medium stores computer readable instructions, e.g., program code, that can be executed by a processor or DSP to carry out one of more of the techniques described above. For example, the computer readable medium can comprise random access memory (RAM), read-only memory (ROM), non-volatile random access memory (NVRAM), electrically erasable programmable read-only memory (EEPROM), flash memory, or the like. The computer readable medium comprises computer readable instructions that when executed in a medical device carry out one or more of the techniques described herein. These and other equivalent embodiments are within the scope of the following claims.

The invention claimed is:

1. An implantable medical device comprising:
a telemetry unit to receive a signal confirming a patient position;
a wavelet transform unit to transform an eleotrogram into a set of wavelets, the electrogram being sensed while the patient is in the confirmed position, the set of wavelets including different subsets of wavelets for different scales; and
a wavelet denoising unit to compare first wavelet coefficients of the wavelets in a first subset to a first threshold, compare second wavelet coefficients of the wavelets in a second subset to a second threshold, the second threshold being different than the first threshold, reduce one or more of the first wavelet coefficients that are less than the first threshold, and reduce one or more of the second wavelet coefficients that are less than the second threshold, wherein the first threshold and the second threshold correspond to the patient being in the confirmed position.

2. The implantable medical device of claim 1, further comprising an inverse wavelet transform unit to transform the set of wavelets into a denoised electrogram following reduction of one or more wavelet coefficients.

3. The implantable medical device of claim 1, wherein the wavelet denoising unit reduces one or more of the first and second wavelet coefficients by selling one or more of the first and second wavelet coefficients to zero.

4. The implantable medical device of claim 1, wherein the wavelet denoising unit compares wavelet coefficients of the wavelets in each respective subset to different thresholds, and reduces any given wavelet coefficient that is less than a respective threshold for the respective subset associated with that given wavelet coefficient.

5. The implantable medical device of claim 1, wherein the telemetry unit receives the first and second thresholds from a programmer prior to transforming the electrogram into the set of wavelets.

6. The implantable medical device of claim 1, wherein the medical device comprises a device selected from the following group: an implantable medical device, an external medical device, a programmer and a diagnostic loop recorder.

7. The implantable medical device of claim 1 wherein the wavelet transform unit and the wavelet denoising unit include analog logic circuits.

8. An implantable medical device comprising:
a telemetry unit to receive a signal confirming a patient position;
a wavelet transform unit to transform a biomedical signal into a set of wavelets, the biomedical signal being sensed while the patient is in the confirmed position, the set of wavelets including different subsets of wavelets for different scales; and
a wavelet denoising unit to compare first wavelet coefficients of the wavelets in a first subset to a first threshold, compare second wavelet coefficients of the wavelets in a second subset to a second threshold, the second threshold being different then the first threshold, reduce one or more of the first wavelet coefficients that are less than the first threshold, and reduce one or more of the second wavelet coefficients that are less than the second threshold, wherein the first threshold and the second threshold correspond to the patient being in the confirmed position.

9. A method comprising:
receiving a signal confirming a patient position;
transforming an electrogram into a set of wavelets, the electrogram being sensed while the patient is in the confirmed position, the set of wavelets including different subsets of wavelets for different scales;
comparing first wavelet coefficients of the wavelets in a first subset to a first threshold;

comparing second wavelet coefficients of the wavelets in a second subset to a second threshold, the second threshold being different then the first threshold;

reducing one or more of the first wavelet coefficients that are less than the first threshold; and reducing one or more of the second wavelet coefficients that are less than the second threshold.

10. The method of claim 9, further comprising transforming the set of wavelets into a denoised electrogram following reduction of one or more wavelet coefficients.

11. The method of claim 9, wherein reducing one or more of the first and second wavelet coefficients comprises setting one or more of the first and second wavelet coefficients to zero.

12. The method of claim 9, further comprising:

comparing wavelet coefficients of the wavelets in each respective subset to different thresholds; and reducing any given wavelet coefficient that is less than a respective threshold for the respective subset associated with that given wavelet coefficient.

13. The method of claim 9, further comprising selecting the first and second thresholds prior to transforming the electrogram into the set of wavelets.

14. The method of claim 13, wherein selecting the first and second thresholds includes adjusting values of the first and second thresholds in response to analysis of one or more denoised electrograms.

15. The method of claim 13, wherein selecting the first and second thresholds includes adjusting values of the first and second thresholds in response to analysis of denoised electrograms sensed while the patient is in the confirmed position.

16. The method of claim 14 wherein the one or more denoised electrograms includes a denoised electrogram sensed with the patient being in a second position, different than the confirmed position.

17. A system comprising:

a first medical device to record electrograms while a patient is in a confirmed position and perform denoising of the electrograms by transforming an electrogram into a set of wavelets, the set of wavelets including different subsets of wavelets for different scales, comparing first wavelet coefficients of the wavelets in a first subset to a first threshold, comparing second wavelet coefficients of the wavelets in a second subset to a second threshold, the second threshold being different then the first threshold, reducing one or more of the first wavelet coefficients that are less than the first threshold, and reducing one or more of the second wavelet coefficients that are less than the second threshold; and a second medial device to confirm the patient position and send a position confirmation signal to the first medical device and to perform threshold estimation to establish the first and second thresholds and send the first and second thresholds to the first medical device.

18. The system of claim 17, wherein the first medical device comprises an implantable medical device and the second medical device comprises a programmer.

19. The system of claim 18, wherein the first medical device comprises an implantable diagnostic loop recorder.

20. A computer readable medium comprising computer readable instructions that when executed:

transform an electrogram into a set of wavelets in response to receiving a signal confirming a patient position, the set of wavelets including different subsets of wavelets for different scales;

compare first wavelet coefficients of the wavelets in a first subset to a first threshold;

compare second wavelet coefficients of the wavelets in a second subset to a second threshold, the second threshold being different then the first threshold;

reduce one or more of the first wavelet coefficients that are less than the first threshold; and reduce one or more of the second wavelet coefficients that are less than the second threshold.

21. The computer readable medium of claim 20, wherein the instructions when executed transform the set of wavelets into a denoised electrogram following reduction of one or more wavelet coefficients.

22. The computer readable medium of claim 20, wherein the instructions when executed reduces one or more of the first and second wavelet coefficients by setting one or more of the first and second wavelet coefficients to zero.

23. The computer readable medium of claim 20, wherein the instructions when executed:

compare wavelet coefficients of the wavelets in each respective subset to different thresholds; and reduce any given wavelet coefficient that is less than a respective threshold for the respective subset associated with that given wavelet coefficient.

24. An apparatus comprising:

means for receiving a signal confirming a patient position;

means for transforming an electrogram into a set of wavelets, the electrogram being sensed while the patient is in the confirmed position, the set of wavelets including different subsets of wavelets for different scales;

means for comparing first wavelet coefficients of the wavelets in a first subset to a first threshold;

means for comparing second wavelet coefficients of the wavelets in a second subset to a second threshold, the second threshold being different then the first threshold;

means for reducing one or more of the first wavelet coefficients that are less than the first threshold; and means for reducing one or more of the second wavelet coefficients that are less than the second threshold.

25. The apparatus of claim 24, further comprising means for transforming the set of wavelets into a denoised electrogram following reduction of one or more wavelet coefficients.

26. The apparatus of claim 24, wherein the means for reducing a respective wavelet coefficient comprises means for setting the respective wavelet coefficient to zero.

27. The apparatus of claim 24, further comprising:

means for comparing wavelet coefficients of the wavelets in each respective subset to different thresholds; and means for reducing any given wavelet coefficient that is less than a respective threshold for the respective subset associated with that given wavelet coefficient.

28. The apparatus of claim 24, further comprising means for receiving selected first and second thresholds prior to transforming the electrogram into the set of wavelets.

29. A system comprising:

means for receiving a signal confirming a patient position;

means for transforming an electrogram into a set of wavelets, the electrogram being sensed while the patient is in the confirmed position, the set of wavelets including different subsets of wavelets for different scales;

means for comparing first wavelet coefficients of the wavelets in a first subset to a first threshold;

means for comparing second wavelet coefficients of the wavelets in a second subset to a second threshold, the second threshold being different then the first threshold;

means for reducing one or more of the first wave let coefficients that are less than the first threshold; and means for reducing one or more of the second wavelet coefficients that are less than the second threshold; and means for selecting the first and second thresholds prior to transforming the electrogram into the set of wavelets.

30. The apparatus of claim 29, wherein the means for selecting includes means for adjusting values of the first and second thresholds in response to analysis of denoised electrograms.

31. A method comprising:

receiving a signal confirming a patient position;

transforming a biomedical signal into a set of wavelets, the biomedical signal being sensed while the patient is in the confirmed position, the set of wavelets including different subsets of wavelets for different scales;

comparing first wavelet coefficients of the wavelets in a first subset to a first threshold;

comparing second wavelet coefficients of the wavelets in a second subset to a second threshold, the second threshold being different then the first threshold;

reducing one or more of the first wavelet coefficients that are less than the first threshold; and reducing one or more of the second wavelet coefficients that are less than the second threshold.

32. The method of claim 31, further comprising transforming the set of wavelets into a denoised biomedical signal following reduction of one or more wavelet coefficients.

33. The method of claim 31, wherein the biomedical signal comprises a signal selected from the group consisting of: an electrogram measured via external sensors, an electrogram measured via implanted sensors, and a signal measured by a biomedical sensor.

34. An implantable medical device comprising:

a telemetry unit to receive a signal confirming a patient position; and an analog logic circuit to transform an electrogram into a set of wavelets, the electrogram being sensed while the patient is in the confirmed position, the set of wavelets including different subsets of wavelets for different scales, and to compare first wavelet coefficients of the wavelets in a first subset to a first threshold, compare second wavelet coefficients of the wavelets in a second subset to a second threshold, the second threshold being different than the first threshold, reduce one or more of the first wavelet coefficients that are less than the first threshold, and reduce one or more of the second wavelet coefficients that are less than the second threshold.

* * * * *

UNITED STATES PATENT AND TRADEMARK OFFICE
CERTIFICATE OF CORRECTION

| | | |
|---|---|---|
| PATENT NO. | : 7,099,714 B2 | Page 1 of 1 |
| APPLICATION NO. | : 10/403915 | |
| DATED | : August 29, 2006 | |
| INVENTOR(S) | : Houben | |

It is certified that error appears in the above-identified patent and that said Letters Patent is hereby corrected as shown below:

Column 12, line 21, change "selling" to --setting--.

Signed and Sealed this

Twenty-sixth Day of December, 2006

JON W. DUDAS
*Director of the United States Patent and Trademark Office*